(12) United States Patent
Tan et al.

(10) Patent No.: US 11,931,256 B1
(45) Date of Patent: Mar. 19, 2024

(54) EXPANDABLE PROSTHETIC HEART VALVE

(71) Applicant: SEVEN SUMMITS MEDICAL, Inc., Casper, WY (US)

(72) Inventors: Jian Tan, Shanghai (CN); Ling Zhou, Shanghai (CN); Kailiang Zhang, Rosemead, CA (US); Albert Yuheng Lee, Rancho Santa Margarita, CA (US)

(73) Assignee: SEVEN SUMMITS MEDICAL, INC., Casper, WY (US)

( * ) Notice: Subject to any disclaimer, the term of this patent is extended or adjusted under 35 U.S.C. 154(b) by 0 days.

(21) Appl. No.: 18/487,991

(22) Filed: Oct. 16, 2023

(30) Foreign Application Priority Data

Sep. 19, 2023 (CN) .......................... 202311214194.0

(51) Int. Cl.
*A61F 2/24* (2006.01)
*A61F 2/00* (2006.01)

(52) U.S. Cl.
CPC .... *A61F 2/2418* (2013.01); *A61F 2002/0081* (2013.01); *A61F 2230/0004* (2013.01); *A61F 2230/0017* (2013.01); *A61F 2250/001* (2013.01); *A61F 2250/0082* (2013.01)

(58) Field of Classification Search
CPC ............ A61F 2/2418; A61F 2002/0081; A61F 2230/0004; A61F 2230/0017; A61F 2250/001; A61F 2250/0082
See application file for complete search history.

(56) References Cited

U.S. PATENT DOCUMENTS

| | | | |
|---|---|---|---|
| 6,454,799 B1 | 9/2002 | Schreck | |
| 11,633,278 B2* | 4/2023 | Noe ....................... | A61F 2/2445 623/1.14 |
| 11,701,224 B1* | 7/2023 | Lee ....................... | A61F 2/0077 623/2.17 |
| 11,806,232 B2* | 11/2023 | Conklin ................ | A61F 2/2409 |
| 2011/0166636 A1 | 7/2011 | Rowe | |
| 2012/0022640 A1 | 1/2012 | Gross | |
| 2016/0074161 A1 | 3/2016 | Bennett | |
| 2019/0133764 A1* | 5/2019 | Carr ...................... | A61F 2/2409 |
| 2020/0229918 A1* | 7/2020 | Pham .................... | A61F 2/2418 |
| 2022/0008233 A1* | 1/2022 | Nia ....................... | A61F 2/915 |

(Continued)

OTHER PUBLICATIONS

Written Opinion of the International Searching Authority, PCT/US23/69265, dated Dec. 12, 2023.

*Primary Examiner* — Suzette J Gherbi
(74) *Attorney, Agent, or Firm* — Treasure IP Group, LLC

(57) ABSTRACT

Disclosed is a prosthetic heart valve, wherein the prosthetic heart valve comprises: a ring-shaped stent, comprising: a mesh structure which allows the stent to be contracted or expanded in a radial direction; and a leaflet structure, comprising a plurality of leaflets, each leaflet is attached to the stent and has a first portion disposed within the stent and a second portion being wrapped to an outer circumferential side of the proximal end of the stent. With a growth of the heart, the stent can be expanded after the prosthetic heart valve is anchored, to allow the prosthetic heart valve to operate in different states, and under at least one of the different states, each leaflet has an excessive portion freely sagging to a position away from the stent along a direction from the distal end to the proximal end, to allow the stent to form a more functional valve.

23 Claims, 10 Drawing Sheets

(56) References Cited

U.S. PATENT DOCUMENTS

| | | | |
|---|---|---|---|
| 2023/0146082 A1* | 5/2023 | Dasi | A61F 2/2418 623/2.17 |
| 2023/0149159 A1* | 5/2023 | Levi | A61F 2/2418 623/2.11 |
| 2023/0372090 A1* | 11/2023 | Hariton | A61F 2/2415 |

* cited by examiner

EXPANDABLE PROSTHETIC HEART VALVE

CROSS-REFERENCE TO RELATED APPLICATION

The present application claims priority to a Chinese patent application No. 202311214194.0, filed on Sep. 10, 2023, and entitled "EXPANDABLE PROSTHETIC HEART VALVE", the entire contents of which are incorporated herein by reference, including the specification, claims, drawings and abstract.

FIELD OF THE DISCLOSURE

The present disclosure relates to a technical field of medical devices, in particular to an expandable prosthetic heart valve which can be operated in different states.

DESCRIPTION OF THE RELATED ART

Native heart valves, such as aortic, pulmonary, mitral, and tricuspid valves, serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or even death, thus it may be eventually necessary to replace a native heart valve with a prosthetic heart valve by surgery or minimally invasive transcatheter implantation.

According to the prior art, after implanting a traditional prosthetic heart valve for replacement of a corresponding native valve, if the patient grows up and the implanted prosthetic heart valve is not suitable in size anymore and cannot be expanded (e.g., current marketed pulmonary prosthetic heart valves are valve conduit that is not expandable), the patient is required to have invasive replacement surgeries every few years, which brings great pain to the patient and increases pressure on medical costs.

Therefore, it is expected to provide a prosthetic heart valve that, to a certain extent, can be expanded to have an expanded size to match the growth of the heart after the prosthetic heart valve was anchored to the heart at an early age.

SUMMARY OF THE INVENTION

In view of this, an objective of the present disclosure is to provide a prosthetic heart valve which is capable to be expanded to have an expanded radial dimension after the prosthetic heart valve is anchored to the heart, so as to allow the prosthetic heart valve to operate in different states without being replaced/removed during the growth of the patient. The prosthetic heart valve according to the present disclosure can be used by a child from around 18 months of age for replacement of a native heart valve and be expandable with the growth of the patient (e.g., a child), so that the patient is not required to replace the implanted prosthetic heart valve by surgery or transcatheter delivery frequently, thus saving medical cost and reducing pain.

According to one aspect of the present disclosure, there is provided a prosthetic heart valve for replacement of a native valve of a heart. The prosthetic heart valve includes:
  a ring-shaped stent, having a distal end and a proximal end in an axial direction, and comprising: a mesh structure as a circumferential sidewall of the stent, which allows the stent to be contracted or expanded in a radial direction; and
  a leaflet structure, comprising a plurality of leaflets, each of which is attached to the stent and has a first portion disposed within the stent and a second portion being wrapped to an outer circumferential side of the proximal end of the stent, wherein the leaflet structure allows blood to flow from the proximal end to the distal end through the prosthetic heart valve and inhibits blood flowing from the distal end to proximal end through the prosthetic heart valve,
  wherein with a growth of the heart, the stent is capable to be expanded to have an expanded radial dimension after the prosthetic heart valve is anchored to the heart, so as to allow the prosthetic heart valve to operate in different states without being replaced,
  wherein an end edge of the second portion of each one of the plurality of leaflets is connected to the stent at a position between the distal end and the proximal end of the stent, without being fixed to the proximal end of the stent, wherein under at least one of the different states, each one of the plurality of leaflets is oversized relative to the stent and has an excessive portion freely sagging to a position away from the stent along a direction from the distal end to the proximal end, so as to allow the stent to form a more functional valve.

In some embodiments, the prosthetic heart valve is for replacement of a native pulmonary valve. In some optional embodiments, the prosthetic heart valve may be used to replace a natural tricuspid valve.

In some embodiments, the stent further comprises a plurality of struts, which are provided for the plurality of leaflets to be attached to, and each extend distally from a proximal end of the mesh structure, wherein the second portion of each one of the plurality of leaflets is wrapped to the outer circumferential side of the proximal end of the stent based on proximal ends of the plurality of struts.

In some embodiments, each one of the plurality of leaflets has a semicircle/semicircle-like shape with an arc edge corresponding to the second portion and a free edge corresponding to the first portion, the free edge is at the distal end and extends between two ends of the arc edge which is wrapped out to the outer circumferential side of the proximal end of the stent, the first portions of the plurality of leaflets are disposed within the stent to operate in a close state for inhibiting blood flowing from the distal end to the proximal end through the prosthetic heart valve when being in contact with each other, or in an open state for allowing blood flowing from the proximal end to the distal end through the prosthetic heart valve when being separated from each other, and the stent has a proximal-end contour matching the arc edges of the plurality of leaflets.

In some embodiments, the mesh structure comprises a plurality of first mesh cells and a plurality of second mesh cells distributed in a circumferential direction, adjacent ones of the plurality of leaflets are connected to form a commissure attached to a corresponding one of the plurality of second mesh cells, two ends of the second portion of each of the plurality of leaflets are attached to two adjacent ones of the plurality of second mesh cells. In some optional embodiments, mesh cells comprised by the mesh structure may be different in shape.

In some embodiments, the plurality of first mesh cells are evenly divided into a number of first-mesh-cell groups, each of which is composed of one or more first mesh cell connected one by one along the circumferential direction, and each two adjacent ones of the first-mesh-cell groups are connected by a corresponding one of the plurality of second mesh cells.

In some embodiments, the plurality of struts are each connected to a corresponding one of the plurality of first mesh cells at the proximal end, for each of the first-mesh-cell groups, lengths of corresponding ones of the plurality of struts gradually reduce from middle to sides.

In some embodiments, each of the plurality of first mesh cells has a spindle-like/diamond-like shape frame; the plurality of first mesh cells are same in size; or each two adjacent mesh cells, one of which is included by the plurality of first mesh cells or the plurality of second mesh cells, share a common frame edge extending from the distal end to the proximal end.

In some embodiments, the stent further comprises a plurality of anchoring cells, which are arranged at a distal end of the mesh structure at intervals and each configured for anchoring to a corresponding anchoring site of the heart.

In some embodiments, each of the plurality of first mesh cells and the plurality of second mesh cells has a distal-end frame edge with a first arch angle pointing to the distal end, and each of the plurality of anchoring cell is connected to a corresponding one of the first arch angles; or each of the plurality of first mesh cells has a proximal-end frame edge with a second arch angle pointing to the proximal end, and each of the plurality of struts is connected to a corresponding one of the second arch angles.

In some embodiments, each of the plurality of second mesh cells provides a concave frame edge at the proximal end for allowing the second portion of a corresponding one of the plurality of leaflet to wrap to the outer circumferential side of the stent over the concave frame edge.

In some embodiments, the concave frame edge comprises: a first connection point at the proximal end, which is connected with an adjacent one of the plurality of first mesh cells; a second connection point at the proximal end, which is connected with another adjacent one of the plurality of first mesh cells; a first frame line and a second frame line, which extend from the first connection point and the second connection point, respectively, and form a corner pointing to the distal end, wherein the second portions of two adjacent ones of the plurality of leaflets are wrapped to the outer circumferential side of the proximal end of the stent over the first frame line and the second frame line, respectively.

In some embodiments, the prosthetic heart valve further comprises a covering layer, which is attached to a surface of the stent and connected with the second portion of each one of the plurality of leaflets. In some optional embodiments, a single-piece/multi-piece covering layer may be attached to an outer and/or inner surface of the stent.

In some embodiments, the plurality of the first mesh cells and the plurality of second mesh cells are entirely covered by the covering layer; and the plurality of the struts are at least partially covered by the second portions of the plurality of leaflets and/or the covering layer.

In some embodiments, a proximal-end portion of the covering layer is sandwiched between the stent and the second portions of the plurality of leaflets.

In some embodiments, the covering layer is sutured with the stent along each distal-end frame edge of the mesh structure and/or each proximal-end frame edge of the mesh structure; wherein the covering layer has a single-piece structure or multi-piece structure. In some optional embodiments, multiple pieces of the covering layer can be connected or spliced together.

In some embodiments, the covering layer has a plurality of openings for allowing the covering layer to be expanded with the stent.

In some embodiments, each of the plurality of openings is a slit or a hole; the plurality of openings are arranged in columns each extending from the distal end to the proximal end; or each of the plurality of first mesh cells corresponds to at least one of the plurality of openings in position.

In some embodiments, the plurality of struts each have a cavity arranged at the proximal end, wherein the cavities of the plurality of struts are connected by suture or wire.

In some embodiments, the covering layer is connected with the stent by suturing based on the cavities of the plurality of the struts.

In some embodiments, the second portion of at least one of the plurality of leaflets is multifolded/pleated at the outer circumferential side of the proximal end of the stent to form folds, which serve as cushion for preventing leakage/backflow and each extend along the struts, so as to be capable of being expanded with the stent.

In some embodiments, the different states of the prosthetic heart valve comprise one or more of following states: a first state, having a first radial dimension for replacing the native valve by implantation; a second state, having a second radial dimension which is adjusted according to the growth of the heart by expansion after the implantation; a third state, having a third radial dimension and serving as a docking adapter for a valve-valve procedure, wherein the second radial dimension is larger than the first radial dimension and smaller than the third radial dimension.

In some embodiments, the implantation is implemented surgically or by transcatheter delivery.

The prosthetic heart valve provided according to the embodiments of the present disclosure is for replacement of a native valve of a heart, and the prosthetic heart valve mainly includes: a stent and a leaflet structure, and the stent has a mesh structure as a circumferential sidewall, so that the stent is expandable at least in a radial direction. With a growth of the heart, the stent is capable to be expanded to have an expanded radial dimension after the prosthetic heart valve is anchored to the heart, so as to allow the prosthetic heart valve to operate in different states without being replaced/removed. Based on these, the prosthetic heart valve according to the embodiments of the present disclosure may keep being functional (as a valve or as an docking adapter) during the patient's growing process (e.g., from 18 month to 16+ years old, or even to 18+ years old), after the prosthetic heart valve is implanted into the heart by surgery or transcatheter delivery, so that the patient is not required to replace the implanted prosthetic heart valve by surgery or transcatheter delivery frequently, thus saving medical cost and reducing pain.

In some applications, the prosthetic heart valve according to the embodiments of the present disclosure is for replacement of a native pulmonary valve, and is capable to be used for treating pulmonary stenosis by an implantation and preventing regurgitation after the implantation without replacing that prosthetic heart valve.

In some optional embodiments, the second portion of at least one of the plurality of leaflets is multifolded/pleated at the outer circumferential side of the proximal end of the stent to form folds extending along the struts, so as to be capable of being expanded with the stent. The multifolded/pleated portion of the leaflets at the proximal end may serve as cushion to prevent leakage/backflow.

In some optional embodiments, the prosthetic heart valve further comprises a covering layer, which is attached to the outer circumferential side of the stent and connected with the second portion of each one of the plurality of leaflets, so as to avoid direct contact between the stent and tissue, which may cause calcification, stress concentration and affect durability. In some embodiments, the covering layer may be designed with various openings (e.g., slits, holes) for future expansion with the expanded stent. In some embodiments, the covering layer may be sutured with the stent along each distal-end frame edge of the mesh structure and/or each proximal-end frame edge of the mesh structure, so as to allow for no impact or pulling of opposing sutures when the prosthetic heart valve is expanded.

In some optional embodiments, the different states of the prosthetic heart valve comprise one or more of following states: a first state (e.g., for a child from 18 month), having a first radial dimension for replacing the native valve by implantation; a second state, having a second radial dimension which is adjusted according to the growth of the heart by expansion after the implantation; a third state, having a third radial dimension and serving as a docking adapter for a valve-valve procedure, where the second radial dimension is larger than the first radial dimension and smaller than the third radial dimension.

BRIEF DESCRIPTION OF THE DRAWINGS

The above and other objects, features and advantages of the present disclosure will become more apparent from the following description of embodiments of the present disclosure with reference to the accompanying drawings, in which.

DETAILED DESCRIPTION OF EMBODIMENTS OF THE DISCLOSURE

Figure 1:
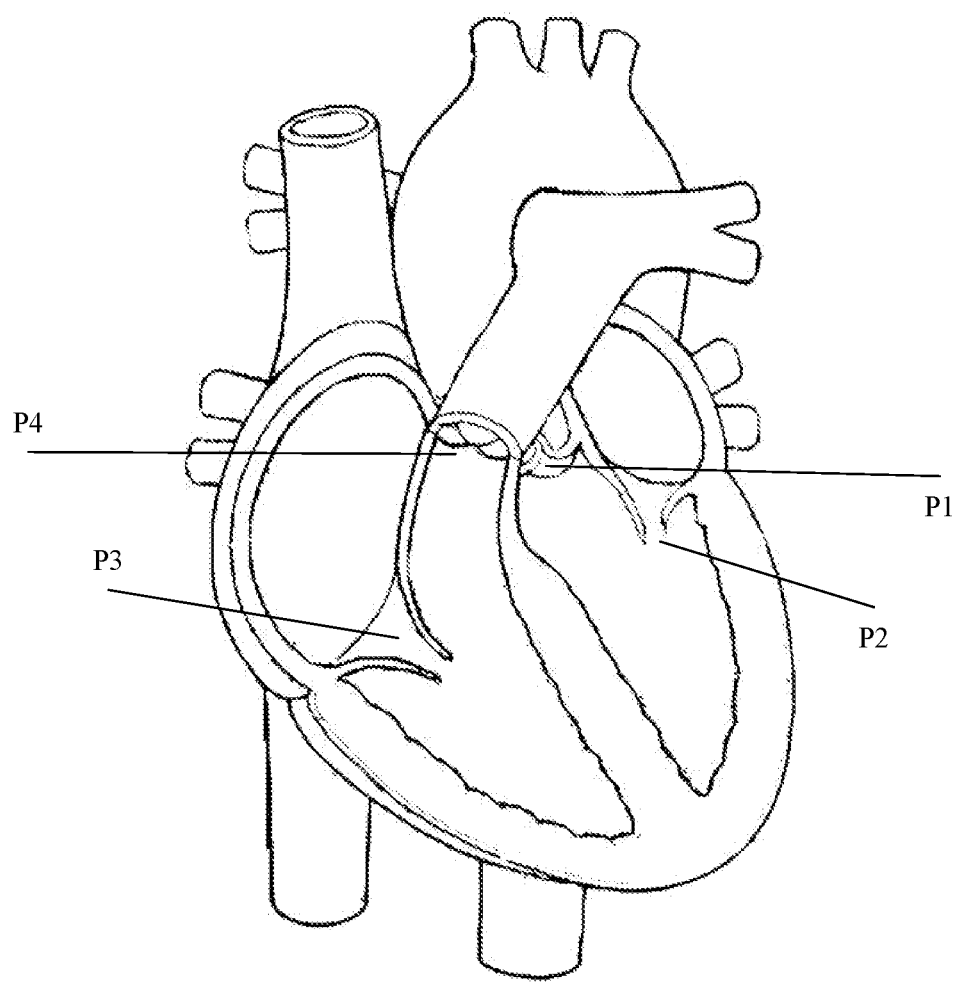
FIG. 1 is a cross section of a heart demonstrating positions of native valves.

The present disclosure will be described in more detail below with reference to the accompanying drawings. Throughout the various figures, like elements are denoted by like reference numerals. For the sake of clarity, various parts in the drawings are not drawn to scale. In addition, some well-known parts may not be shown in the figure.

Several exemplary embodiments of prosthetic heart valves are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

Application Scenarios

FIG. 1 is a cross section of a heart demonstrating positions of native valves.

As shown in FIG. 1, a healthy heart is four-chambered and comprises a left atrium, a right atrium, a left ventricle, and a right ventricle. The left and right sides of the heart are separated by a wall generally referred to as a septum. The native valves of the heart include: a mitral valve P2 for connecting the left atrium to the left ventricle, an aortic valve P1 for connecting the left ventricle to the aorta, a tricuspid valve P3 for connecting the right atrium to the right ventricle, and a pulmonary valve P4 for connecting the right ventricle to the pulmonary artery.

If a native valve is diseased, the prosthetic heart valve can be implanted into the diseased position by surgery or transcatheter implantation, so as to replace that natural valve with the prosthetic heart valve.

After implanting a traditional prosthetic heart valve for replacement of a corresponding native valve, if the patient grows up and the implanted prosthetic heart valve is not suitable in size anymore and cannot be expanded (e.g., current marketed pulmonary prosthetic heart valves are valve conduit that cannot be expandable), the patient is required to have invasive replacement surgeries every few years, which brings great pain to the patient and increases pressure on medical costs.

Specifically, for replacing pulmonary valve P4, traditional prosthetic heart valves are mainly developed for adults with stable heart size, and based on those traditional prosthetic heart valves, after the implantation for replacement of a pulmonary valve P4, pulmonary regurgitation is a common postoperative sequela following repair of tetralogy of Fallot (TOF).

According to the embodiments of the present disclosure, there is provided a prosthetic heart valve, wherein the prosthetic heart valve, or at least part of it, has a mesh structure, which allows the prosthetic heart valve to be contracted or expanded in a radial direction, so that the prosthetic heart valve is capable to be expanded to have an expanded radial dimension after the prosthetic heart valve is anchored/implanted to the heart, thus allowing the prosthetic heart valve to operate in different states without being replaced/removed.

In some applications where the prosthetic heart valve is used for replacing pulmonary valve, compared with the prior art, the prosthetic heart valve according to embodiments of the present disclosure can treat pulmonary stenosis through a single implantation and prevent regurgitation after the implantation without being replaced or removed by another surgery.

Basic Structures

Figure 2:
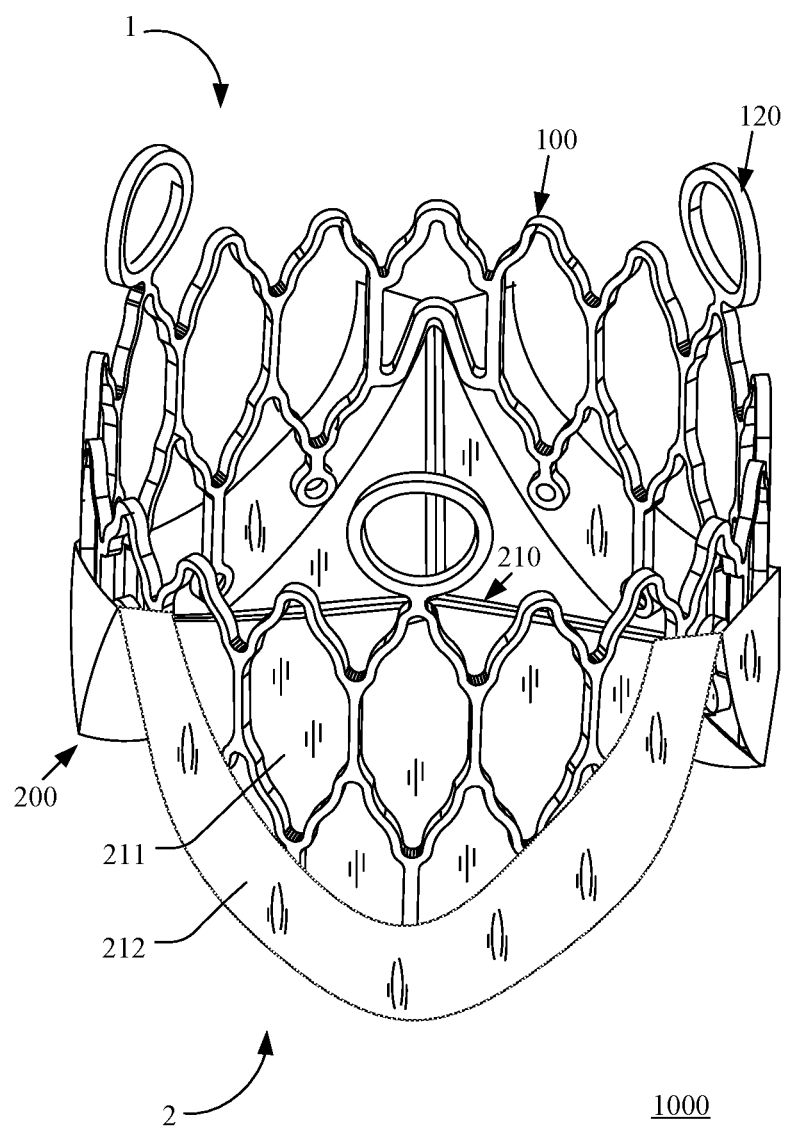
FIG. 2 shows a schematic structural diagram of a prosthetic heart valve according to an embodiment of the present disclosure.
Figure 9:
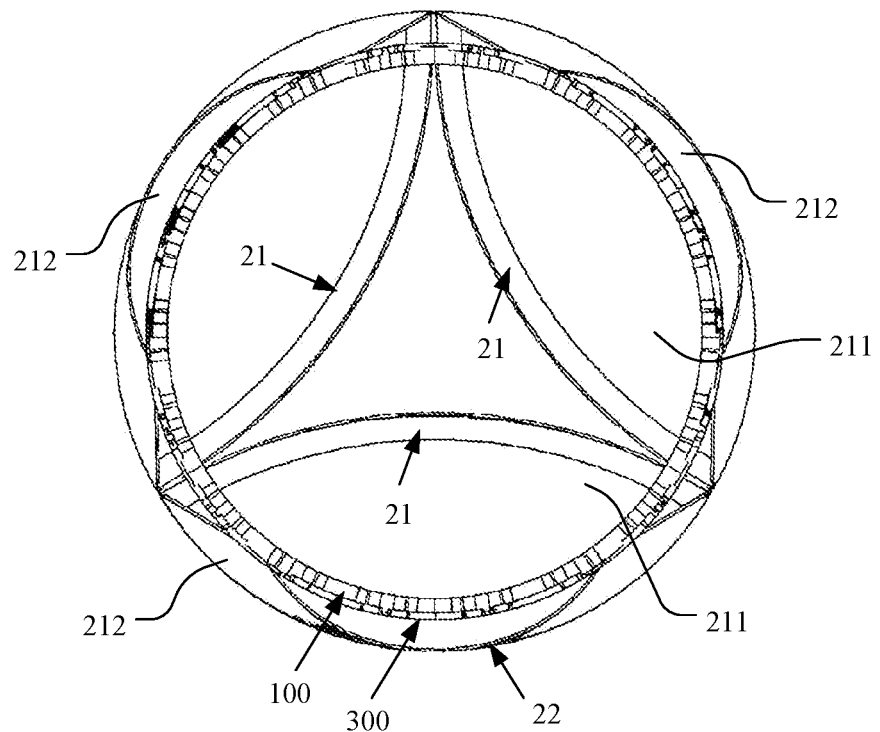
FIG. 9 shows a top-view schematic structural diagram from the distal end of a prosthetic heart valve with leaflets under open state according to an embodiment of the present disclosure.

FIG. 2 shows a schematic structural diagram of a prosthetic heart valve according to an embodiment of the present disclosure. FIG. 9 shows a top-view schematic structural diagram from the distal end of a prosthetic heart valve with leaflets under open state according to an embodiment (e.g., as shown in FIGS. 2 and 11) of the present disclosure.

Figure 10:
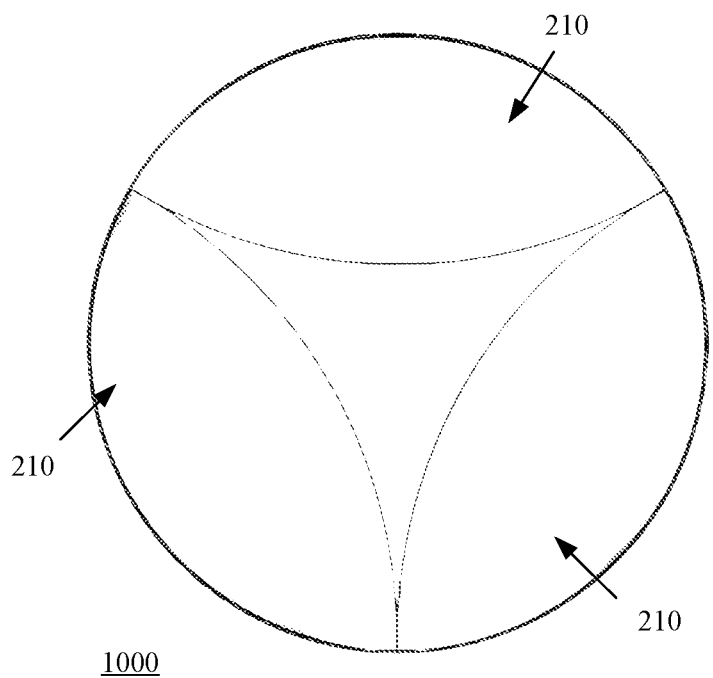
FIG. 10 shows a bottom-view schematic structural diagram from the proximal end of a prosthetic heart valve with leaflets under open state according to an embodiment of the present disclosure.
Figure 11:
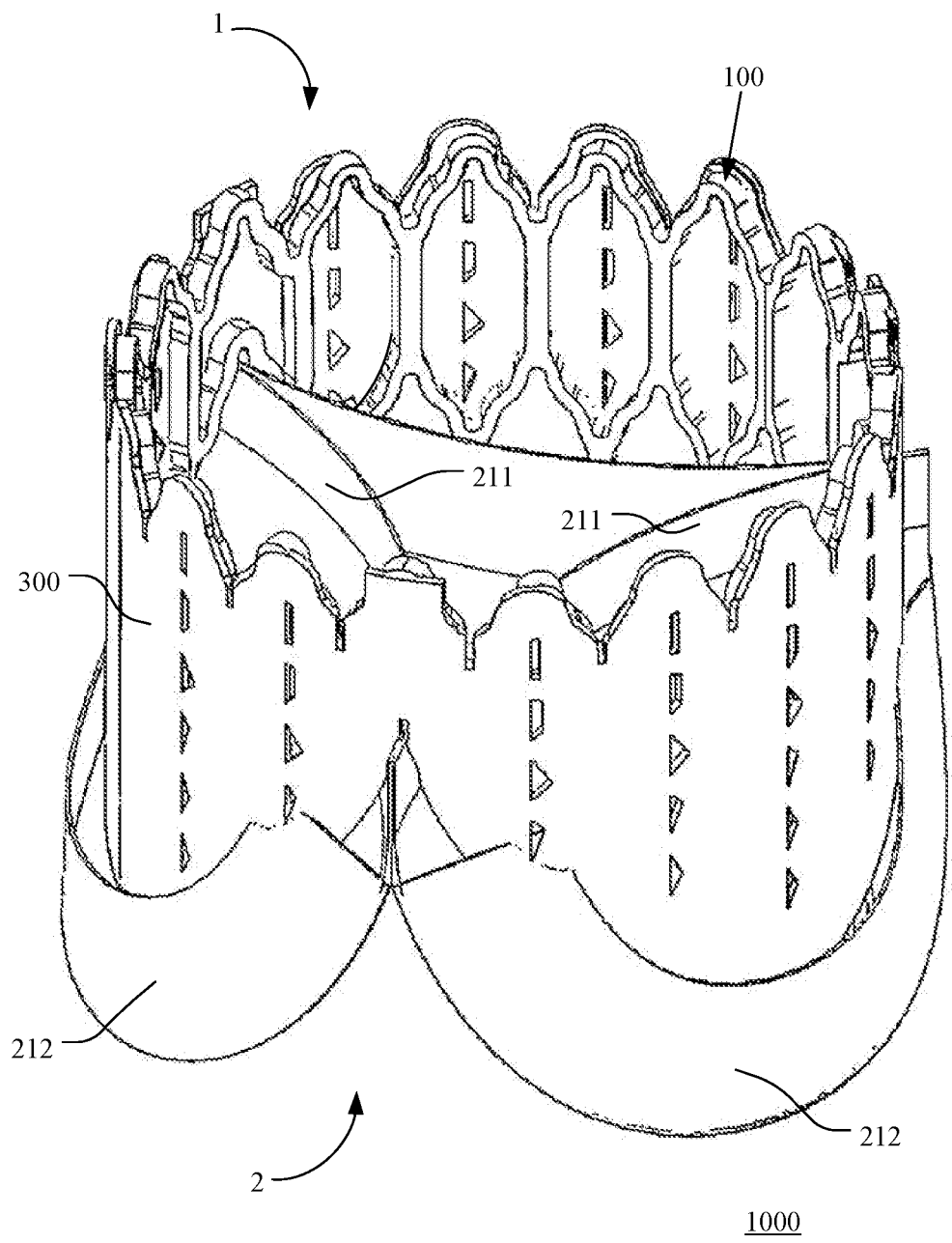
FIG. 11 shows a schematic structural diagram of a prosthetic heart valve without anchoring cell according to another embodiment of the present disclosure.

FIG. 10 shows a bottom-view schematic structural diagram from the proximal end of a prosthetic heart valve with leaflets under open state according to an embodiment (e.g., as shown in FIGS. 2 and 11) of the present disclosure.

As shown in FIG. 2, the prosthetic heart valve 1000 for replacement of a native valve of a heart mainly comprises a ring-shaped stent 100, and a leaflet structure 200 attached to the stent 100.

The stent 100 is used to anchor the prosthetic heart valve 1000 at a target implantation position (e.g., aortic valve position, pulmonary valve position, mitral valve position, tricuspid valve position). The stent 100 can be annular, and may have a distal end 1 and a proximal end 2 opposite to each other in the axial direction.

For the prosthetic heart valve 1000 to be size-adaptable, the stent 100 uses a mesh design with materials such as cobalt nickel alloy or annealed nitinol, etc. As an example, the stent 100 at least comprises a mesh structure allowing the stent 100 to be contracted or expanded in a radial direction, thus with a growth of the heart, the stent 100 is capable to be expanded to have an expanded radial dimension after the prosthetic heart valve is anchored to the heart, so as to allow the prosthetic heart valve to operate in different states without being replaced. In some embodiments, a diameter of the stent 100 may range from 2 mm to 55 mm, preferably from 10 mm to 30 mm.

For example, the different states of the prosthetic heart valve 1000 may comprise one or more of following states: a first state, having a first radial dimension for replacing the native valve by implantation; a second state, having a second radial dimension which is adjusted according to the growth of the heart by expansion after the implantation; a third state, having a third radial dimension and serving as a docking adapter for a valve-valve procedure, where the second radial dimension is larger than the first radial dimension and smaller than the third radial dimension.

Under the first state, the prosthetic heart valve 1000 can be operated for replacing the diseased native valve of a patient (e.g., a child from 18 months), for example, by surgical implantation or interventional method (transcatheter). Because the stent 100 has the mesh structure as a circumferential sidewall, the prosthetic heart valve 1000 can be compressed into a delivery apparatus for transcatheter applications.

After the implantation, with the growth of the child, the heart may need a larger valve to maintain its function, the implanted prosthetic heart valve 1000 can be expanded, for example, by balloon dilation, to allow the prosthetic heart valve 1000 to operate in the second state without replacing the prosthetic heart valve 1000 by another valve through another implantation.

Further, with the growth of the child, if the implantation position of the heart is grown to a size exceeding a certain size that cannot be functionally supported by the prosthetic heart valve 1000 as a valve, the implanted prosthetic heart valve 1000 can be further expanded from the second state to operate in the third state as a docking adaptor for being connected to another valve structure in a future valve-in-valve procedure, without being replaced or removed.

Based on the prosthetic heart valve 1000 according to the embodiments of the present disclosure, various tests, including stent expansion test, valve expansion test, valve pulsating flow test, valve fatigue test, and so on, have been performed. Based on these feasibility tests, several size levels can be set for the different states.

As a first example, the first radial dimension of the first state may be Size 12 (may represent that an outside diameter of the stent is 12 mm) which can allow the prosthetic heart valve 1000 to provide good enough hemodynamics; the second radial dimension of the second state may be expanded from Size 12 up to Size 15 (may represent that an outside diameter of the stent is 15 mm), which can also provide good enough hemodynamics; and the third radial dimension of the third state may be expanded to Size 16 (may represent that an outside diameter of the stent is 16 mm) and beyond or Size 22 (may represent that an outside diameter of the stent is 22 mm) and beyond, for supporting the prosthetic heart valve 1000 as a docking adaptor/station for a valve-valve procedure. For example, when the prosthetic heart valve 1000 serves as a docking adaptor, a replacement pulmonary valve may be delivered into the heart by going through a catheter, and a balloon on a tip of the catheter is capable to be expanded to press the new pulmonary valve into the prosthetic heart valve 1000 serving as a docking adaptor which exists in the heart.

As a second example, the first radial dimension of the first state may be Size 14 (may represent that an outside diameter of the stent is 14 mm) which can allow the prosthetic heart valve 1000 to provide good enough hemodynamics; the second radial dimension of the second state may be expanded from Size 14 up to almost Size 18 (may represent that an outside diameter of the stent is 18 mm), which can also provide good enough hemodynamics; and the third radial dimension of the third state may be expanded to Size 19 (may represent that an outside diameter of the stent is 19 mm) and beyond or Size 22 (may represent that an outside diameter of the stent is 22 mm) and beyond, for supporting the prosthetic heart valve 1000 as a docking adaptor/station for a valve-valve procedure.

As a third example, the first radial dimension of the first state may be Size 16 which can allow the prosthetic heart valve 1000 to provide good enough hemodynamics; the second radial dimension of the second state may be expanded from Size 16 up to almost Size 18, which can also provide good enough hemodynamics; and the third radial dimension of the third state may be expanded to Size 19 and beyond or Size 22 and beyond, for supporting the prosthetic heart valve 1000 as a docking adaptor/station for a valve-valve procedure.

It should be noted that, if the implantation position of the heart of the patient (a child or an adult) is already grown to a size matching the second state of the prosthetic heart valve 1000 before the implantation, the prosthetic heart valve 1000 can be expanded to the second state through the implantation. The ranges of expansion of the prosthetic heart valve 1000 are designed to provide enough hemodynamics.

In some embodiments, the prosthetic heart valve 1000 is for replacement of a native pulmonary valve. In the prior art, after a valve is implanted, stenosis and regurgitation may be developed, and another device may be used for remedy. According to the prior art, for example, a valve conduit replacement may be used for fixing stenosis and regurgitation, or a patch may be used for solving stenosis problem.

However, the valve conduit cannot be expanded to match a grown size of the implantation position, and the patch may further introduce regurgitation. Compared with the prior art, the prosthetic heart valve 1000 according to embodiments of the present disclosure can treat pulmonary stenosis through a single implantation and prevent regurgitation after the implantation without being replaced or removed by another surgery.

However, the present disclosure is not limited thereto. In other embodiments, the prosthetic heart valve 1000 may also be used to replace other native valve structure such as a native tricuspid valve.

In some optional embodiments, material of the stent 100 can be medical stainless steel, nickel-titanium alloy (nitinol) or cobalt-chromium alloy, etc.

In some optional embodiments, a wall thickness along the radial direction of the stent 100 may be 0.1 to 1 mm, e.g., 0.2 mm to 0.6 mm.

As shown in FIG. 2, the leaflet structure 200 includes a plurality of leaflets 210, each of which is attached to the stent and has a first portion 211 disposed within the stent 100 and a second portion 212 being wrapped to an outer circumferential side of a proximal end of the stent 100. The leaflet structure 200 allows one-way flow of blood from the proximal end 2 to the distal end 1 through the prosthetic heart valve 1000 and inhibits blood flowing from the distal end 1 to the proximal end 2 through the prosthetic heart valve 1000. As an example, as shown in FIG. 2, the leaflet structure 200 may be formed by three leaflets 210 connected with each other, and each leaflet 210 is attached to a corresponding position of the stent 100.

In some optional embodiments, material of each leaflet 210 may be bovine pericardium, porcine pericardium or polymer material. In some optional embodiments, a wall thickness of each leaflet may be 0.1-0.7 mm, e.g., 0.2-0.45 mm.

In some optional embodiments, as shown in FIG. 2, the stent 100 of the prosthetic heart valve 1000 may further include one or more anchoring cell 120, each of which is arranged at a distal end of the mesh structure 110 and configured for anchoring to a corresponding anchoring site (e.g., pulmonary valve position) of the heart. As an example, more than one anchoring cells are arranged at the distal end of the mesh structure 110 at intervals. As an example, each anchoring cell 120 may be provided with a connection cavity (e.g., hole, slit, or slot) 30 at the distal end 1. As an example, each anchoring cell 120 may have a ring-like structure which extends along the axial direction of the stent 100 and allows suture or wire to pass through for anchoring. However, each connection cavity of the anchoring cells is not limited to the shape shown in the figures, but also can be designed in round, square, oval, polygon, irregular shape, etc. It should be understood that, in some applications, the stent 100 of the prosthetic heart valve 1000 may be implemented with no anchoring cell 120, depending on actual needs and designs.

Figure 12:
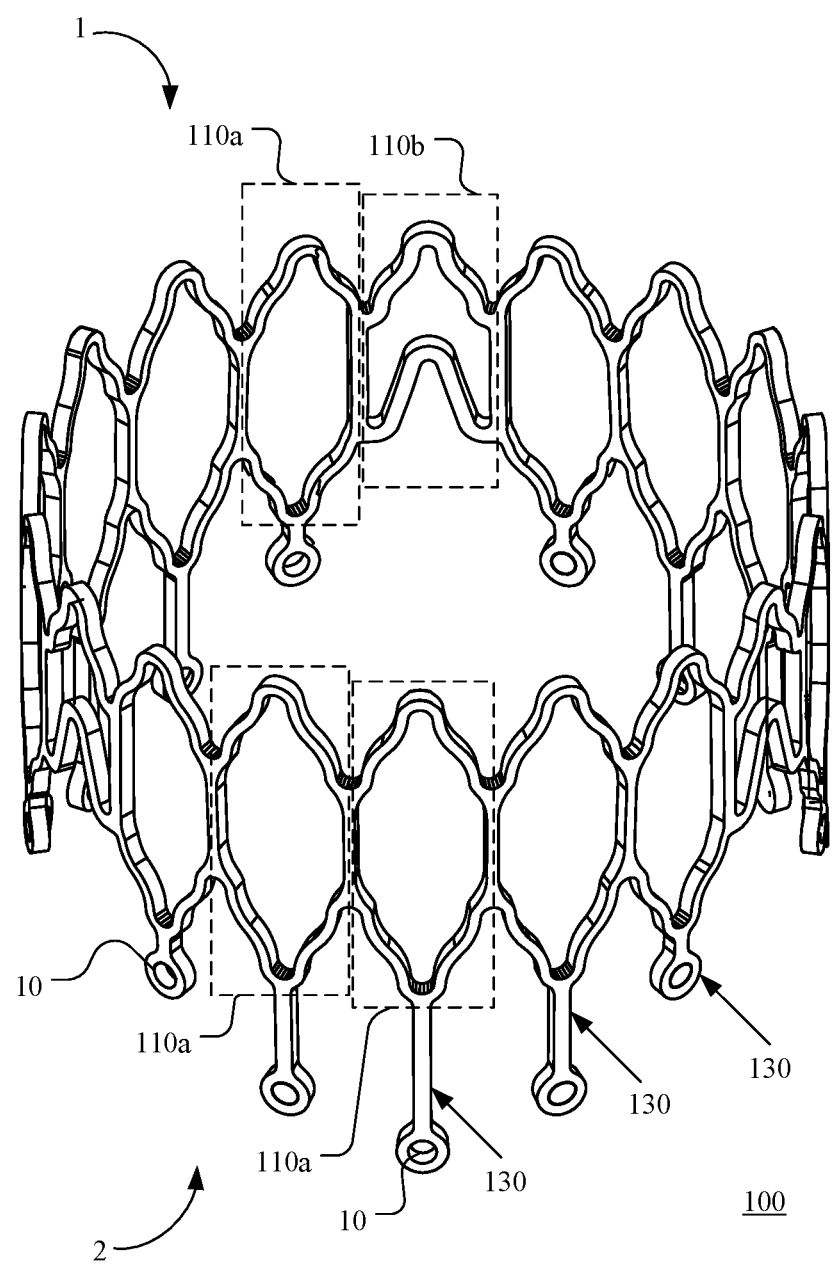
FIG. 12 is a schematic structural diagram of the stent of the prosthetic heart valve without anchoring cell according to an embodiment of the present disclosure.

In some optional embodiments, the mesh structure 110 itself can be used to anchor to the corresponding anchoring site of the heart, so that it is not necessary to further provide any anchoring cell other than the mesh structure 110 (as shown in FIG. 11), thus simplifying the structure of the stent 100 (as shown in FIG. 12). As an example, a mesh cell of the mesh structure 110 may allow suture or wire to pass through for anchoring.

Figure 3:
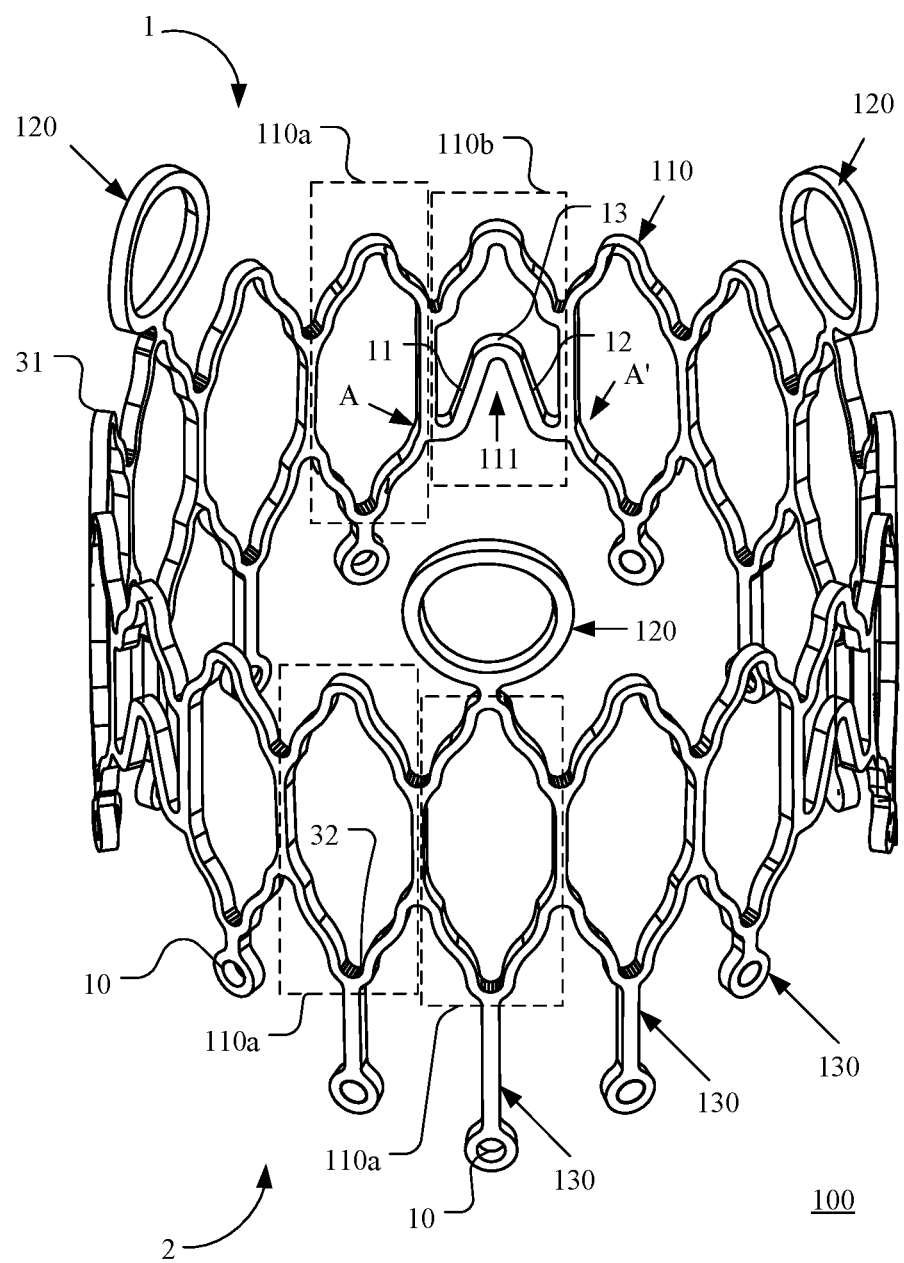
FIG. 3 is a schematic structural diagram of the stent of the prosthetic heart valve according to an embodiment of the present disclosure.

FIG. 3 is a schematic structural diagram of the stent of the prosthetic heart valve according to an embodiment (e.g., as shown in FIG. 2) of the present disclosure. FIG. 11 shows a schematic structural diagram of a prosthetic heart valve without anchoring cell according to another embodiment of the present disclosure. FIG. 12 is a schematic structural diagram of the stent of the prosthetic heart valve according to an embodiment (e.g., as shown in FIG. 11) of the present disclosure.

As shown in FIG. 3 and FIG. 12, the stent 100 includes the mesh structure 110, which comprises a plurality of first mesh cells 110a and a plurality of second mesh cells 110b distributed along a circumferential direction. The plurality of second mesh cells 110b respectively correspond to the commissures 20 formed by adjacent leaflets 210 in location, such that the commissures 20 can be secured to the stent 100 based on the second mesh cells 110b. The number of second mesh cells 110b may be greater than/equal to the number of leaflets 210.

In some embodiments, the stent 100 may further include a plurality of struts 130, which are provided for the plurality of leaflets 210 to be attached to, and each extend distally from a proximal end of the mesh structure 110 to the proximal end 2 of the stent 100 by a certain length. Proximal ends of the plurality of struts 130 are connected to provide a structural support for the second portion 212 of each one of the plurality of leaflets 210 to be wrapped to the outer circumferential side of the proximal end of the stent 100.

As an example, a width of each strut 130 may be 0.1 mm to 1 mm, e.g., 0.2 mm to 0.7 mm.

As an example, at least one of the struts 130 can serve as a flexible cantilever that may not affect the collapsing and expanding of the stent 100, for allowing further expansion. As a cantilever, each strut 130 has a fixed end, which is permanently attached to the mesh structure 110, and a flexible end, extending to the proximal end 2, thus in one variation, each of the struts 130 may have at least three degrees of freedom of movement, including two translational movements and one rotation movement. The two translational movements are selected from three translational movements along x, y, and z axis directions, for example, x and y axis directions. The x, y, and z directions are defined in a coordinate where the connecting point between the mesh structure 110 and the fixed end of the strut 130 as an origin. The rotational movement is selected from two rotational movements, a spin and a revolution. Spin is defined as a rotation around an axis of itself, to allow the flexible end of the strut 130 to rotate around itself. Revolution is defined as for the flexible end of the strut 130 to rotate around an axis of not itself, for example an axis of a cylinder shape of the mesh structure circumferential sidewall, or an axis or pseudo-axis formed when the flexible end of the strut 130 is lifted and wind around rotate. In another variation, each of the plurality of struts 130 can further translation along an additional direction, for example, along the z axis. In still another variation, the each of the plurality of struts 130 can further rotate along an additional axis. The movement in three or four degrees of freedom allow for further expansion under the different states of the valve 1000, and may have minimal impact on the structure of the prosthetic heart valve 1000. As an example, at least one of the struts 130 may be slightly deformed (e.g., bended, twisted, and/or tilted based on the fixed end as a fulcrum), such that the flexible end of each of the struts 130 may deviated from its original position to a subsequent position.

As an example, the mesh structure 110 and the plurality of struts 130 can be integrally formed of a same material. The material may have enough toughness to allow the mesh structure 110 to collapse and expand, and allow the flexible end of each strut to have at least three degrees of freedom, including translations along x, y and z axis directions.

As an example, at least one of the struts 130 is provided with a cavity 10. For example, as shown in FIGS. 2 to 3, the cavity 10 may be a hole disposed at the proximal end 2 of the stent 100. Each strut 130 can still move in at least three degrees of freedom from blood pressure. At the same time, the covering(s) according to embodiments of the present disclosure may also be flexible enough to support movement.

In some optional embodiments, the plurality of first mesh cells 110a are evenly divided into a number of first-mesh-cell groups, each of which is composed of one or more first mesh cell 110a connected one by one along the circumferential direction, and each two adjacent ones of the first-mesh-cell 110a groups are connected by a corresponding one of the plurality of second mesh cells 110b.

In some embodiments with the struts 130, two ends of the second portion 212 of each of the plurality of leaflets 210 are attached to two adjacent ones of the plurality of second mesh cells 110b and at least one of the plurality of struts 130. The plurality of struts 130 may be each connected to a corresponding one of the plurality of first mesh cells 110a at the proximal end 2, and for each of the first-mesh-cell groups, lengths of corresponding ones of the plurality of struts 130 may gradually reduce from middle to sides.

In some optional embodiments, as shown in FIGS. 3 and 12, each of the plurality of first mesh cells 110a may have a ring-like/spindle-like/diamond-like shape frame. As an example, in order to facilitate collapsing and expanding, each first mesh cell 110a may has a shuttle-like shape with opposite ends pointing to the proximal and distal ends, respectively.

In some optional embodiments, the plurality of first mesh cells 110a may all be the same or similar in size/shape, and the plurality of second mesh units 110b may all be the same or similar in size/shape. However, embodiments of the present disclosure are not limited thereto, and in some other embodiments, the mesh cells comprised by the mesh structure may have different shapes.

In some optional embodiments, each two adjacent mesh cells, one of which is included by the plurality of first mesh cells 110a or the plurality of second mesh cells 110b, share a common frame edge extending from the distal end 1 to the proximal end 2. That is, as shown in FIGS. 3 and 12, two adjacent first mesh cells 110a may share a common edge, and each second mesh cell 110b and an adjacent one of the first mesh cells 110a may share a common edge provided with a corresponding first point A or a corresponding second point A'.

In some implementations, every two adjacent second mesh cells 110b may be spaced apart by at least one first mesh cell 110a. As an example, as shown in FIGS. 3 and 12, the number of the first mesh cells 110a arranged between every two adjacent second mesh cells 110b may be constant. As a further example, the number of the first mesh cells 110a arranged between every two adjacent second mesh cells 110b may be odd, and/or, the lengths of the struts 130 of the first mesh cells 110a located between two adjacent second mesh cells 110b may sequentially decrease from the middle to both sides in the circumferential direction of the stent 100, such that the position of the flexible end of each strut 130 can be adapted to the position of the second portion 212 of the corresponding leaflet 210 at the proximal end 2, which is beneficial for the struts 130 to provide support for the leaflets 210.

In some optional embodiments, as shown in FIGS. 3 and 12, each of the plurality of first mesh cells 110a and the plurality of second mesh cells 110b has a distal-end frame edge with a first arch angle 31 pointing to the distal end 1.

In some embodiments with anchoring cells 120, as shown in FIG. 3, each of the plurality of anchoring cell 120 may be connected to a corresponding one of the first arch angles 31.

In some optional embodiments, as shown in FIGS. 3 and 12, each of the plurality of first mesh cells 110a, has a proximal-end frame edge with a second arch angle 32 pointing to the proximal end 2, and each of the plurality of struts 130 may be connected to a corresponding one of the second arch angles 32.

In some optional embodiments, as shown in FIGS. 3 and 12, each of the plurality of second mesh cells 110b provides a concave frame edge 111 at the proximal end 2 for allowing the second portion 212 of a corresponding one of the plurality of leaflet 210 to wrap to the outer circumferential side of the stent 100 over the concave frame edge 111.

In some optional embodiments, as shown in FIGS. 3 and 12, the concave frame edge 111 includes: the first connection point A at the proximal end 2, which is connected with an adjacent one of the plurality of first mesh cells; the second connection point A' at the proximal end 2, which is connected with another adjacent one of the plurality of first mesh cells 110a; a first frame line 11 and a second frame line 12, which extend from the first connection point A and the second connection point A', respectively, and form a corner 13 pointing to the distal end 1. As an example, the corner 13 may be in arc shape, sharp-angled shape, or other shape, which includes shapes not specifically described in the present disclosure.

The second portions 212 of two adjacent ones of the plurality of leaflets 210 are wrapped to the outer circumferential side of the proximal end of the stent 100 over the first frame edge 11 and the second frame edge 12, respectively.

It should be noted that the cavities 10 mentioned in the present disclosure are not limited to be the circular holes shown in FIG. 3, but can also be designed as rectangle, oval, polygon, irregular shape or other shapes. In some alternative implementations, the cavities may also be implemented as slits and slots of various shapes as well. In some preferred embodiment, the slits may permit an easy insertion or penetration.

In addition, as an optional embodiment, the covering layer may have a single-piece structure or a multi-piece structure (the multi pieces of the covering layer may be connected or spliced to each other), and the covering layer with the single-piece or multi-piece structure may be attached to an inner surface and/or an outer surface of the stent.

Figure 4:
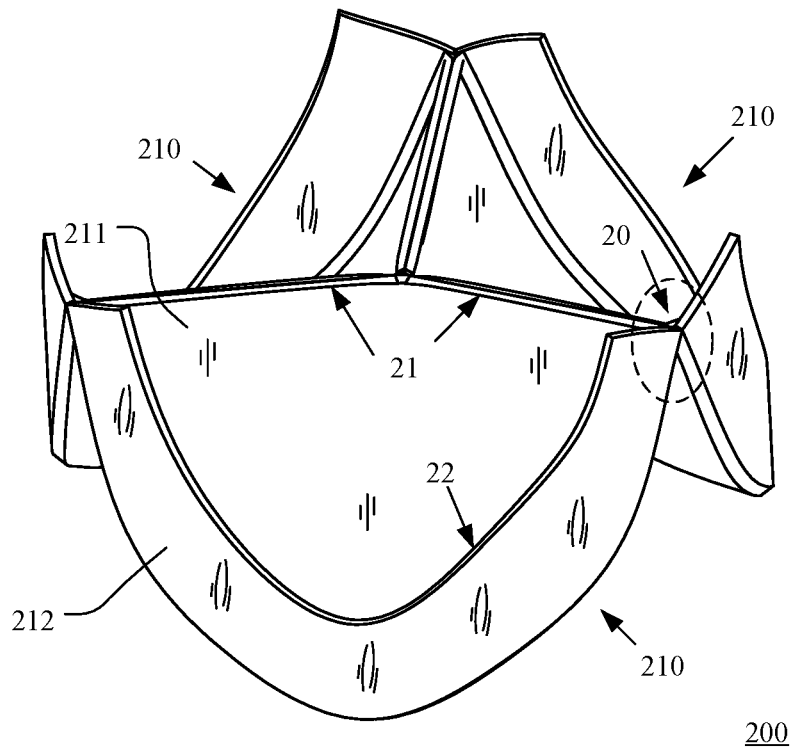
FIG. 4 shows a schematic diagram of a leaflet structure of an embodiment of the present disclosure.
Figure 5:
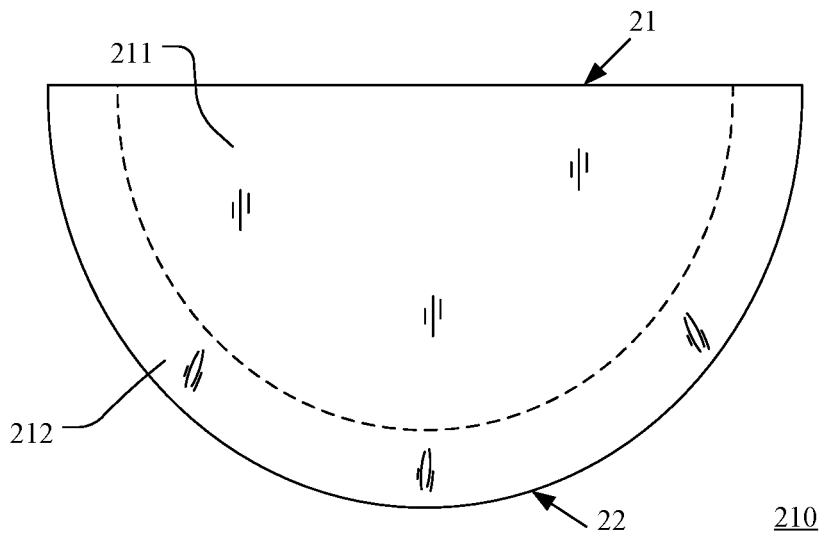
FIG. 5 shows a flattened view of a structure of a single leaflet according to an embodiment of the present disclosure.

FIG. 4 shows a schematic diagram of a leaflet structure of an embodiment of the present disclosure. FIG. 5 shows a flattened view of a structure of a single leaflet according to an embodiment of the present disclosure.

As shown in FIGS. 2, 4 and 5, the leaflet structure 200 includes the plurality of leaflets 210, configured to allow blood to flow from the proximal end 2 to the distal end 1 through the prosthetic heart valve 1000 and inhibit blood flowing from the distal end 1 to proximal end 2 through the prosthetic heart valve 1000.

As a typical example, as shown in FIGS. 2 and 4, the leaflet structure 200 comprises three angled and interconnected leaflets 210, and the present disclosure is mainly illustrated by this example. However, the present disclosure does not limit the number of leaflets 210 in the leaflet structure 200, and the leaflet structure 200 may also consist of two or more than three leaflets 210.

As shown in FIG. 5, a flattened shape of one single leaflet 210 is, for example, semicircular or similar to a semicircular shape, which has an arc edge 22 corresponding to the second portion 212 and a free edge 21 corresponding to the first portion 211, the free edge is at the distal end 1 and extends between two ends of the arc edge 22 which is wrapped out to the outer circumferential side of the proximal end of the stent 100 and attached to at least one of a corresponding one of the second mesh cells 110b, a corresponding one of the first mesh cells 110a, and a corresponding one of the struts 130.

The first portions 211 of the plurality of leaflets 210 are disposed within the stent 100 to operate in a close state for inhibiting blood flowing from the distal end 1 to the proximal end 2 through the prosthetic heart valve 1000 when the free edges 21 of the plurality of leaflets 210 are in contact with each other, or in an open state for allowing blood flowing from the proximal end 2 to the distal end 1 through the prosthetic heart valve 1000 when the free edges 21 of the plurality of leaflets 210 are at least partially separated from each other.

In some embodiments, the stent 100 may have a proximal-end contour matching the arc edges 22 of the plurality of leaflets 210.

In some embodiments, each end of each free edges 21 may be secured with an adjacent free edge 21 of another leaflet 210 to form a commissure 20, so that adjacent leaflets 210 can be connected with each other at the commissure 20, as shown in FIG. 2. The commissures 20 formed by the plurality of leaflets 210 are attached to the stent 100, as an example, the commissures 20 formed by the plurality of leaflets 210 can be attached to the plurality of second mesh cells 110b, respectively.

As an example, as shown in FIGS. 2 and 4, the second portion 212 of each leaflet 210 can be folded from an inner space surrounded by the stent 100 to an outer side of the stent 100 based on one or more of the struts 130, so that the second portion 212 of the leaflets can be attached to the outer side of the stent 100.

In some embodiments, the plurality of the struts 130 may be entirely/partially covered by the second portions 212 of the plurality of leaflets 210 at a certain height along the axial direction.

Based on the exemplary stent structures referring to FIG. 4, for each leaflet 210, the first frame line 11 and the second frame line 12 included by the concave frame edge 111 may form a corner 13 as a junction pointing to the distal end 1, so as to allow the second portion 212 of that leaflet 210 to be folded from the inner side to the outer side of the stent 100 based on a curved contour (formed according to the struts 130, the first frame line 11 and the second frame line 12 of a corresponding second mesh cell 110b) at the proximal end 2 of the stent 100, and at the same time, allow the first portions 211 of the leaflets 210 to be attached to the opposite side (i.e., inner side) of the stent 100.

In order to stably secure the leaflet structure 200 to the stent 100 and avoid direct contact between the stent (e.g., metal) and tissue, which may cause calcification, stress concentration and affect durability, one or more covering layer may be provided circumferentially on the outside of the stent 100 serving as a connection for the leaflets 210.

Figure 6:
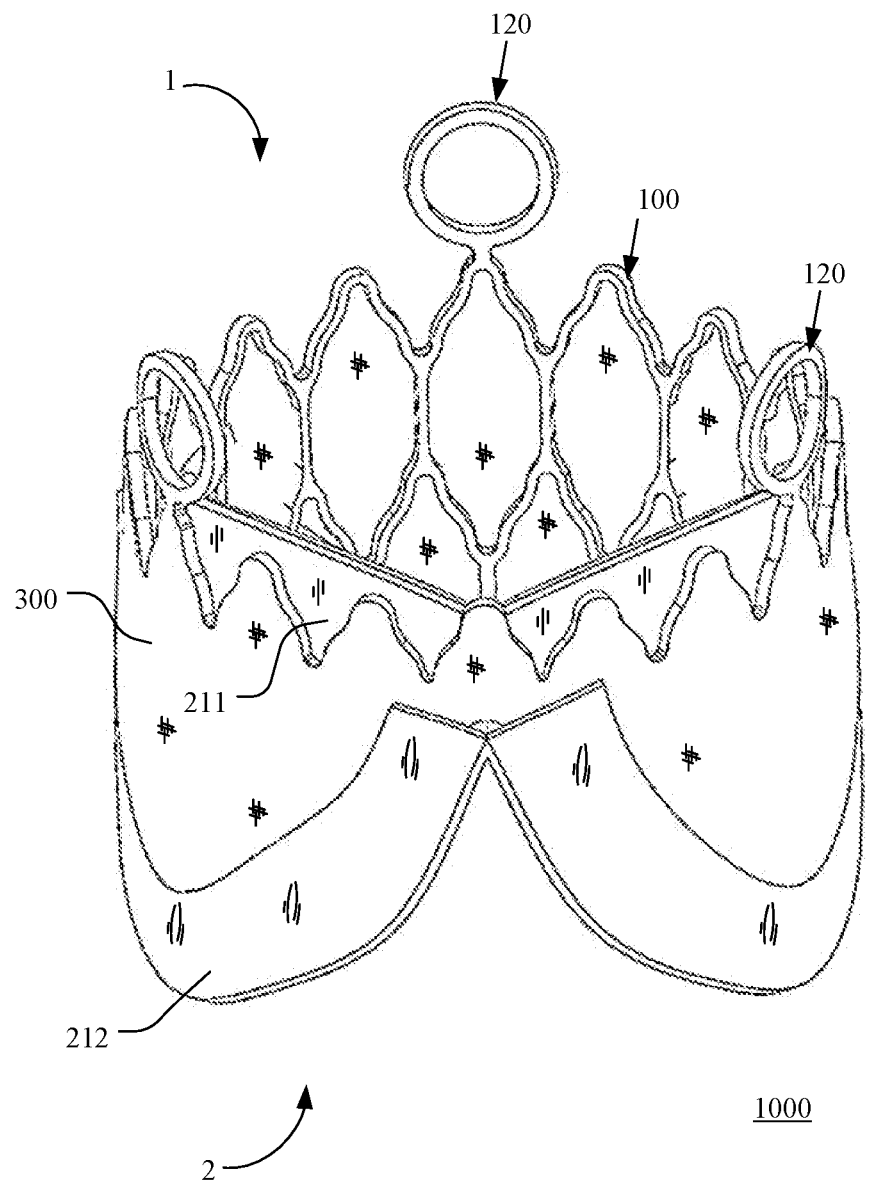
FIG. 6 shows a position relation between a covering layer and the stent according to an embodiment of the present disclosure.
Figure 7A:
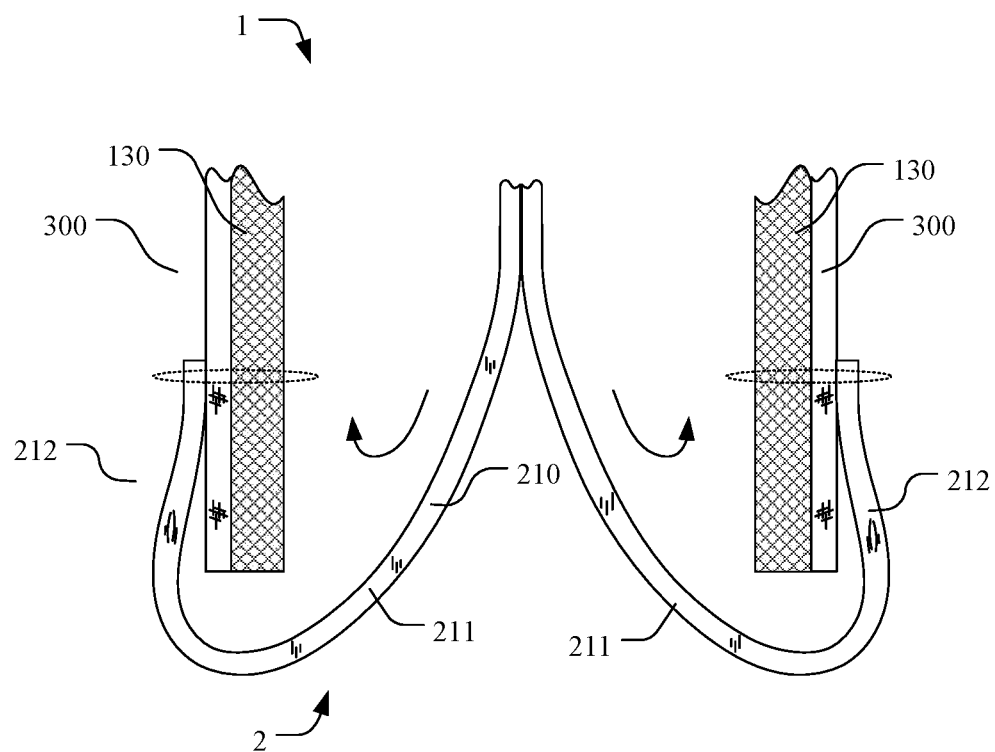
FIG. 7a shows a cross-sectional structure diagram of the prosthetic heart valve at a position of one of the struts as shown in FIG. 6 along the radial direction of the stent.
Figure 7B:
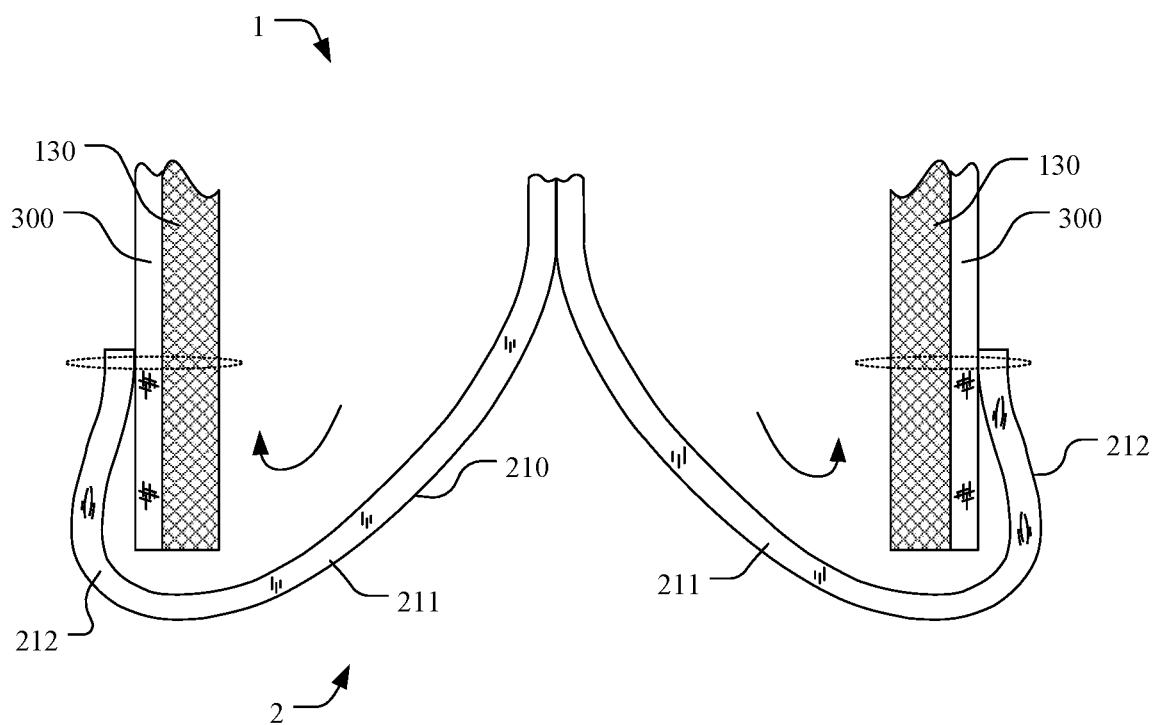
FIG. 7b shows a cross-sectional structure diagram of the prosthetic heart valve at a position of one of the struts along the radial direction of the stent as shown in FIG. 6 under an expanded state.
Figure 8:
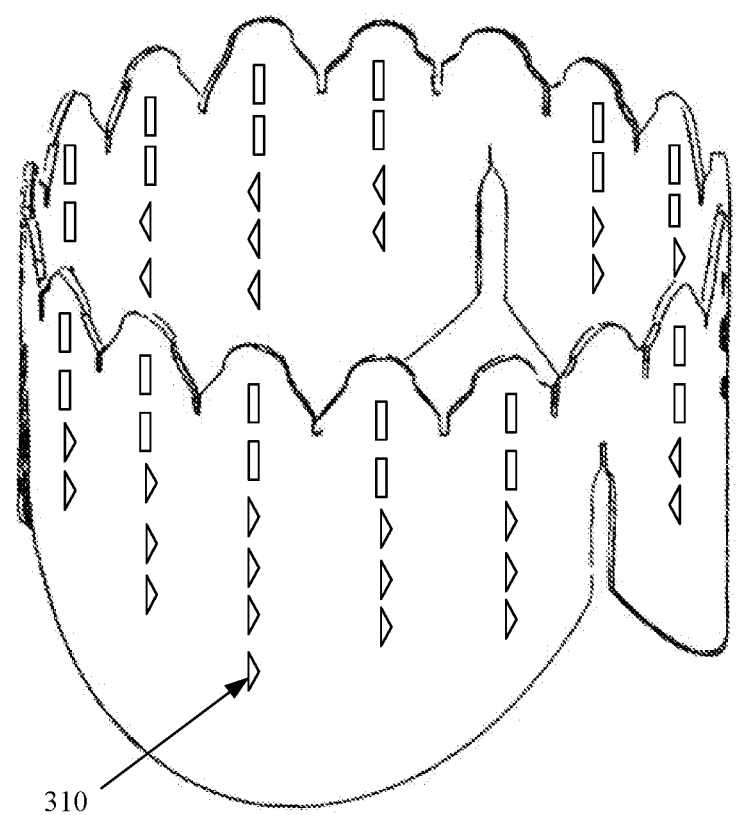
FIG. 8 shows a structure of the covering layer as shown in FIGS. 6, 7a and 7b.

FIG. 6 shows a position relation between a covering layer and the stent according to an embodiment of the present disclosure. FIG. 7a shows a cross-sectional structure diagram of the prosthetic heart valve at a position of one of the struts as shown in FIG. 6 along the radial direction of the stent. FIG. 7b shows a cross-sectional structure diagram of the prosthetic heart valve at a position of one of the struts along the radial direction of the stent as shown in FIG. 6 under an expanded state. FIG. 8 shows a structure of the covering layer as shown in FIGS. 6, 7a and 7b.

In some optional embodiments, a covering layer 300 is provided as a base for stitching, in order to secure the leaflets 210 to the stent 100. The covering layer 300 may have a skirt-like shape, as shown in FIGS. 6 and 8, and is attached to the outer circumferential side of the stent 100 and connected with the second portion 212 of each one of the plurality of leaflets 210.

In some embodiments, the plurality of the first mesh cells 110a and the plurality of second mesh cells 110b may be entirely/partially covered by the covering layer 300.

In some embodiments, the plurality of the struts 130 may be entirely/partially covered by the covering layer 300.

As an example, the covering layer 300 may has a distal-end contour matching the distal-end contour (including distal-end arches of the first mesh cells and distal-end arches of the second mesh cells) of the mesh structure 110 of the stent 100, and has a proximal-end contour matching the proximal-end contour of the stent 100, that is, the covering layer 300 may axially extend from an distal edge of the mesh structure 110 to the proximal end of the struts 130 and the concave frame edge 111 of the second mesh cells 110b, so as to entirely cover the mesh structure 110 and the struts 130.

In some optional embodiments, as shown in FIGS. 6, 7a and 7b, at least a proximal-end portion of the covering layer 300 may be sandwiched between the plurality of leaflets 210 and the plurality of struts 130, so that the second portions 212 of the leaflets and the covering layer 300 can be connected together by applying blanket, locking and/or other type of stitching through the struts, so as to be attached to the stent 100.

In some embodiments, the covering layer 300 can be sutured with the stent 100 along the distal-end contour (including distal-end arches of the first mesh cells and distal-end arches of the second mesh cells) of the mesh structure 110 of the stent 100 and/or the proximal-end contour of the stent 100.

As an example, the covering layer 300 is sutured with the stent 100 along each distal-end frame edge (e.g., each distal-end arch) of the mesh cells (110a, 110b) in the mesh structure 110 and/or each proximal-end frame edge (e.g., each proximal-end arch) of the mesh cells (110a, 110b) in the mesh structure 110, so that sutures arranged during the implantation using this suturing method may not be impacted or pulled when the prosthetic heart valve 1000 is expanded to another state (e.g., second/third state mentioned above) with a larger radial dimension.

Further, as an example, the covering layer 300 and the second portion 212 of each leaflet 210 may also be sutured along one or more of the struts 130.

In some simplified embodiments, the covering layer 300 may be the only covering layer attached to the stent 100.

According to embodiments of the present disclosure, referring to FIGS. 2, 4 and 6, the leaflets 210 are oversized compared with the stent 100 under the first state and/or the second state, so that the leaflet structure 200 can be expanded with the stent 100 after the implantation without losing its function or being destroyed during the expansion.

In some embodiments, as shown in FIGS. 7a and 7b, an end edge of the second portion of each one of the plurality of leaflets 210 is connected to the stent 100 at a position between the distal end 1 and the proximal end 2 of the stent 100, without being fixed to the most proximal end of the stent, and each one of the plurality of leaflets 210 is oversized relative to the stent under at least one of the different states, so that under the at least one (first state and/or second state) of the different states, at least one of the plurality of leaflets 210 freely hangs/sags to a position away from the stent 100 along a direction from the distal end to the proximal end, so as to allow the leaflets 210 to be capable of being expanded with the stent 100 with no constraint at the proximal end of the stent 100, that is, allowing further expansion of the stent 100 for forming a more functional valve. Thus, the freedom at the bottom allows the excessive leaflet material to sag to form a more functional valve at a position away from the stent 100, and the freedom may provide space to accommodate the excessive leaflet material so it can form a more functional valve (in the expandable prosthetic heart valve, the excessive leaflet can be positioned at the bottom of the stent, allowing for more freedom at the bottom, this arrangement reduces the occurrence of wiggly or jammed leaflets at the distal end, resulting in improved valve opening and a more functional valve).

In some embodiments, the oversized leaflets 210, which are wrapped circumferentially over the struts 130 at the proximal end 2, can be multifolded/pleated, and sutured along the struts 130 and/or the covering layer 300 to allow for future expansion. For example, the second portion 212 of at least one of the plurality of leaflets 210 can be multifolded/pleated at the outer circumferential side of the proximal end of the stent 100 to form folds extending along the struts 130, so as to be capable of being expanded with the stent 100 under different states mentioned above. Further, the multifolded/pleated portions of the leaflets 210 at the proximal end can also serve as cushion to prevent leakage/backflow.

According to embodiments of the present disclosure, as shown in FIG. 8, the covering layer 300 may be provided with a plurality of openings 310, so that the covering layer 300 can be expanded with the stent 100 after the implantation without losing its function or being destroyed during the expansion under the different states.

The plurality of openings 310 may be slits, holes or the like, and may all be designed in a same shape or be designed in various shapes.

As an example, one or more of the openings 310 may be a triangular hole, for example, having at least one angle pointing to the distal/proximal end. However, the shapes disclosed herein are not intended to limit the present disclosure, one or more the openings can also be designed in other kinds of shapes such as a round/oval hole, rectangular hole/slit, etc.

As an example, the plurality of openings 310 may be arranged in columns each extending from the distal end 1 to the proximal end 2.

In some embodiments, each of the plurality of first mesh cells 110a may correspond to at least one of the plurality of openings 310 in position.

In some optional embodiments, the covering layer 300 may be manufactured as a one-piece covering layer for maintaining its ability for further expansion. Material of the covering layer 300 can be PET or other material which promotes endothelialization. In some optional embodiments, thickness of the covering layer 300 may be 0.05-0.5 mm, e.g., 0.1-0.25 mm.

According to embodiments of the present disclosure, an assembling method of the prosthetic heart valve in any embodiment of the present disclosure is also provided, and detailed steps can be performed according to descriptions of embodiments of the prosthetic heart valve mentioned above, which will not be repeated here.

The prosthetic heart valve provided according to the embodiments of the present disclosure is for replacement of a native valve of a heart, and the prosthetic heart valve mainly includes: a stent and a leaflet structure, and the stent has a mesh structure as a circumferential sidewall, so that the stent is expandable at least in a radial direction. With a growth of the heart, the stent is capable to be expanded to have an expanded radial dimension after the prosthetic heart valve is anchored to the heart, so as to allow the prosthetic heart valve to operate in different states without being replaced/removed. Based on these, the prosthetic heart valve according to the embodiments of the present disclosure may keep being functional (as a valve or as an docking adapter) during the patient's growing process (e.g., from 18 month to 16+ years old, or even to 18+ years old), after the prosthetic heart valve is implanted into the heart by surgery or transcatheter delivery, so that the patient is not required to replace the implanted prosthetic heart valve by surgery or transcatheter delivery frequently, thus saving medical cost and reducing pain.

In some applications, the prosthetic heart valve according to the embodiments of the present disclosure is for replacement of a native pulmonary valve, and is capable to be used for treating pulmonary stenosis by an implantation and preventing regurgitation after the implantation without replacing that prosthetic heart valve.

In some optional embodiments, the second portion of at least one of the plurality of leaflets is multifolded/pleated at the outer circumferential side of the proximal end of the stent to form folds extending along struts, so as to be capable of being expanded with the stent. The multifolded/pleated portion of the leaflets at the proximal end may serve as cushion to prevent leakage/backflow.

In some optional embodiments, the prosthetic heart valve further comprises a covering layer, which is attached to the outer circumferential side of the stent and connected with the second portion of each one of the plurality of leaflets, so as to avoid direct contact between the stent and tissue, which may cause calcification, stress concentration and affect durability. In some embodiments, the covering layer may be designed with various openings (e.g., slits, holes) for future expansion with the expanded stent. In some embodiments, the covering layer may be sutured with the stent along each distal-end frame edge of the mesh structure and/or each proximal-end frame edge of the mesh structure, so as to allow for no impact or pulling of opposing sutures when the prosthetic heart valve is expanded.

In some optional embodiments, the different states of the prosthetic heart valve comprise one or more of following states: a first state (e.g., for a child from 18 month), having a first radial dimension for replacing the native valve by implantation; a second state, having a second radial dimension which is adjusted according to the growth of the heart by expansion after the implantation; a third state, having a third radial dimension and serving as a docking adapter for a valve-valve procedure, where the second radial dimension is larger than the first radial dimension and smaller than the third radial dimension.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim all that comes within the scope and spirit of these claims and their equivalents.

What is claimed is:

1. A prosthetic heart valve for replacement of a native valve of a heart, wherein the prosthetic heart valve comprises:
a ring-shaped stent (100), having a distal end (1) and a proximal end (2) in an axial direction, and comprising:
a mesh structure (110) as a circumferential sidewall of the stent, which allows the stent to be contracted or expanded in a radial direction; and
a leaflet structure (200), comprising a plurality of leaflets (210), each of which is attached to the stent and has a first portion (211) disposed within the stent and a second portion (212) being wrapped to an outer circumferential side of the proximal end of the stent, wherein the leaflet structure allows blood to flow from the proximal end to the distal end through the prosthetic heart valve and inhibits blood flowing from the distal end to proximal end through the prosthetic heart valve,
wherein with a growth of the heart, the stent is capable to be expanded to have an expanded radial dimension after the prosthetic heart valve is anchored to the heart, so as to allow the prosthetic heart valve to operate in different states without being replaced,
wherein an end edge of the second portion of each one of the plurality of leaflets is connected to the stent at a position between the distal end and the proximal end of the stent, without being fixed to the proximal end of the stent,
wherein each of the plurality of leaflets is oversized relative to the stent and has an excessive portion (210e) freely sagging to a position away from the stent along a direction from the distal end to the proximal end, under one state, so as to allow the stent to form a more functional valve.

2. The prosthetic heart valve according to claim 1, wherein the prosthetic heart valve is for replacement of a native pulmonary valve.

3. The prosthetic heart valve according to claim 1, wherein the stent further comprises a plurality of struts (130), which are provided for the plurality of leaflets to be attached to, and each extend distally from a proximal end of the mesh structure,
wherein the second portion of each one of the plurality of leaflets is wrapped to the outer circumferential side of the proximal end of the stent based on proximal ends of the plurality of struts.

4. The prosthetic heart valve according to claim 3, wherein,
each one of the plurality of leaflets has a semicircle/semicircle-like shape with an arc edge corresponding to the second portion and a free edge corresponding to the first portion, the free edge is at the distal end and extends between two ends of the arc edge which is wrapped out to the outer circumferential side of the proximal end of the stent,
the first portions of the plurality of leaflets are disposed within the stent to operate in a close state for inhibiting blood flowing from the distal end to the proximal end through the prosthetic heart valve when being in contact with each other, or in an open state for allowing blood flowing from the proximal end to the distal end through the prosthetic heart valve when being separated from each other, and
the stent has a proximal-end contour matching the arc edges of the plurality of leaflets.

5. The prosthetic heart valve according to claim 3, wherein the mesh structure comprises a plurality of first mesh cells (110a) and a plurality of second mesh cells (110b) distributed in a circumferential direction,
adjacent ones of the plurality of leaflets are connected to form a commissure (20) attached to a corresponding one of the plurality of second mesh cells, two ends of the second portion of each of the plurality of leaflets are attached to two adjacent ones of the plurality of second mesh cells.

6. The prosthetic heart valve according to claim 5, wherein the plurality of first mesh cells are evenly divided into a number of first-mesh-cell groups, each of which is composed of one or more first mesh cell connected one by one along the circumferential direction, and each two adjacent ones of the first-mesh-cell groups are connected by a corresponding one of the plurality of second mesh cells.

7. The prosthetic heart valve according to claim 6, wherein the plurality of struts are each connected to a corresponding one of the plurality of first mesh cells at the proximal end,
for each of the first-mesh-cell groups, lengths of corresponding ones of the plurality of struts gradually reduce from middle to sides.

8. The prosthetic heart valve according to claim 5, wherein,
each of the plurality of first mesh cells has a spindle-like/diamond-like shape frame;
the plurality of first mesh cells are same in size; or
each two adjacent mesh cells, one of which is included by the plurality of first mesh cells or the plurality of second mesh cells, share a common frame edge extending from the distal end to the proximal end.

9. The prosthetic heart valve according to claim 5, wherein, the stent further comprises a plurality of anchoring cells (120), which are arranged at a distal end of the mesh structure at intervals and each configured for anchoring to a corresponding anchoring site of the heart.

10. The prosthetic heart valve according to claim 9, wherein,
each of the plurality of first mesh cells and the plurality of second mesh cells has a distal-end frame edge with a first arch angle pointing to the distal end, and each of the plurality of anchoring cell is connected to a corresponding one of the first arch angles; or
each of the plurality of first mesh cells has a proximal-end frame edge with a second arch angle pointing to the proximal end, and each of the plurality of struts is connected to a corresponding one of the second arch angles.

11. The prosthetic heart valve according to claim 5, wherein each of the plurality of second mesh cells provides a concave frame edge at the proximal end for allowing the second portion of a corresponding one of the plurality of leaflet to wrap to the outer circumferential side of the stent over the concave frame edge.

12. The prosthetic heart valve according to claim 11, wherein the concave frame edge comprises:
a first connection point (A) at the proximal end, which is connected with an adjacent one of the plurality of first mesh cells;
a second connection point (A') at the proximal end, which is connected with another adjacent one of the plurality of first mesh cells;
a first frame line (11) and a second frame line (12), which extend from the first connection point and the second connection point, respectively, and form a corner pointing to the distal end, wherein the second portions of two adjacent ones of the plurality of leaflets are wrapped to the outer circumferential side of the proximal end of the stent over the first frame line and the second frame line, respectively.

13. The prosthetic heart valve according to claim 5, further comprising a covering layer (300), which is attached to a surface of the stent and connected with the second portion of each one of the plurality of leaflets.

14. The prosthetic heart valve according to claim 13, wherein
the plurality of the first mesh cells and the plurality of second mesh cells are entirely covered by the covering layer; and
the plurality of the struts are at least partially covered by the second portions of the plurality of leaflets and/or the covering layer.

15. The prosthetic heart valve according to claim 13, wherein a proximal-end portion of the covering layer is sandwiched between the stent and the second portions of the plurality of leaflets.

16. The prosthetic heart valve according to claim 13, wherein the covering layer is sutured with the stent along each distal-end frame edge of the mesh structure and/or each proximal-end frame edge of the mesh structure;
wherein the covering layer has a single-piece structure or multi-piece structure.

17. The prosthetic heart valve according to claim 13, wherein the covering layer has a plurality of openings (310) for allowing the covering layer to be expanded with the stent.

18. The prosthetic heart valve according to claim 17, wherein,
each of the plurality of openings is a slit or a hole;
the plurality of openings are arranged in columns each extending from the distal end to the proximal end; or
each of the plurality of first mesh cells corresponds to at least one of the plurality of openings in position.

19. The prosthetic heart valve according to claim 13, wherein the plurality of struts each have a cavity (10) arranged at the proximal end, wherein the cavities of the plurality of struts are connected by suture or wire to provide the structural support for the plurality of leaflets.

20. The prosthetic heart valve according to claim 19, wherein the covering layer is connected with the stent by suturing based on the cavities of the plurality of the struts.

21. The prosthetic heart valve according to claim 3, wherein the second portion of at least one of the plurality of leaflets is multifold/pleated at the outer circumferential side of the proximal end of the stent to form folds, which serve as cushion for preventing leakage/backflow and each extend along the struts, so as to be capable of being expanded with the stent.

22. The prosthetic heart valve according to claim 1, wherein the different states of the prosthetic heart valve comprise one or more of following states:
a first state, having a first radial dimension for replacing the native valve by implantation;
a second state, having a second radial dimension which is adjusted according to the growth of the heart by expansion after the implantation;
a third state, having a third radial dimension and serving as a docking adapter for a valve-valve procedure,
wherein the second radial dimension is larger than the first radial dimension and smaller than the third radial dimension.

23. The prosthetic heart valve according to claim 1, wherein the implantation is implemented surgically or by transcatheter delivery.

* * * * *